United States Patent
Bae et al.

(10) Patent No.: US 10,266,858 B2
(45) Date of Patent: Apr. 23, 2019

(54) **MICROORGANISM OF THE GENUS *CORYNEBACTERIUM* WITH ENHANCED ABILITY TO PRODUCE L-ARGININE AND METHOD FOR PRODUCING L-ARGININE USING THE SAME**

(71) Applicant: CJ Cheiljedang Corporation, Seoul (KR)

(72) Inventors: Hyun Ae Bae, Seoul (KR); Min Gyeong Kang, Seoul (KR); Han Hyoung Lee, Seoul (KR); Hye Won Kim, Gyeonggi-do (KR); Sung Gun Lee, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 14/785,759

(22) PCT Filed: Apr. 23, 2014

(86) PCT No.: PCT/KR2014/003570
§ 371 (c)(1),
(2) Date: Oct. 20, 2015

(87) PCT Pub. No.: WO2014/175663
PCT Pub. Date: Oct. 30, 2014

(65) Prior Publication Data
US 2016/0145661 A1 May 26, 2016

(30) Foreign Application Priority Data
Apr. 23, 2013 (KR) .................. 10-2013-0044723

(51) Int. Cl.
| | | |
|---|---|---|
| C12P 13/10 | (2006.01) | |
| C12N 9/14 | (2006.01) | |
| C12N 9/88 | (2006.01) | |
| C07K 14/34 | (2006.01) | |
| C12N 9/10 | (2006.01) | |

(52) U.S. Cl.
CPC .............. *C12P 13/10* (2013.01); *C07K 14/34* (2013.01); *C12N 9/1096* (2013.01); *C12N 9/88* (2013.01); *C12Y 206/01001* (2013.01); *C12Y 403/01001* (2013.01)

(58) Field of Classification Search
CPC .......... C12P 13/005; C12P 13/10; C12N 9/14; C12N 9/88; C12N 1/20; C12N 9/10
USPC ......................................... 435/252.3, 69.1, 6
See application file for complete search history.

(56) References Cited

U.S. PATENT DOCUMENTS

| 7,759,094 B2 | 7/2010 | Rieping |
|---|---|---|
| 8,952,217 B2 * | 2/2015 | Puzio ................. C12N 15/8214 |
| | | 435/320.1 |

FOREIGN PATENT DOCUMENTS

| EP | 0318663 A1 | 6/1989 |
|---|---|---|
| JP | S62-079788 A | 4/1987 |
| JP | A05-030977 | 2/1993 |
| JP | 2001-046082 A | 2/2001 |
| JP | 2011-182779 A | 9/2011 |
| JP | A2012-044869 | 3/2012 |
| JP | 2010-515468 A | 5/2013 |
| WO | WO 2005/064000 | 7/2005 |
| WO | WO 2006/092449 | 9/2006 |
| WO | WO2008-088148 A1 | 7/2008 |
| WO | WO2012-061653 | 5/2012 |

OTHER PUBLICATIONS

International Search Report dated Aug. 26, 2014 in PCT/KR2014/003570.
Dou et al. (Jul. 23, 2011) Appl. Biochem. Biotechnol. 165 (3-4):845-855, "Improvement of L-arginine production by overexpression of a bifunctional ornithine acetyltransferase in *Corynebacterium crenatum*".
Ikeda et al. (Mar. 2009) Appl Environ. Microbiol. 75(6):1635-1641, "Reengineering of a *Corynebacterium glutamicum* L-arginine and L-citrulline producer".
Menkel et al. (Mar. 1989) Appl. Environ. Microbiol. 55(3):684-688, "Influence of increased aspartate availability on lysine formation by a recombinant strain of *Corynebacterium glutamicum* and utilization of fumarate".
Database WPI, Week 199311, Thomson Scientific, London, GB; AN 1993-087959, XP002761389, XP002761389, & JP H05 30977 A (Mitsubishi Petrochemical, Co Ltd) Feb. 9, 1993 (Feb. 9, 1993)—abstract.
EP Search Report dated Sep. 14, 2016 in EP 14788335.9.

* cited by examiner

*Primary Examiner* — Maryam Monshipouri
(74) *Attorney, Agent, or Firm* — Adsero IP

(57) ABSTRACT

The present invention relates to a microorganism of the genus *Corynebacterium*, which has an enhanced activity of aspartate ammonia-lyase and/or aspartate aminotransferase, and thus has an enhanced ability to produce L-arginine, and to a method of producing L-arginine using the microorganism of the genus *Corynebacterium*.

11 Claims, 1 Drawing Sheet
Specification includes a Sequence Listing.

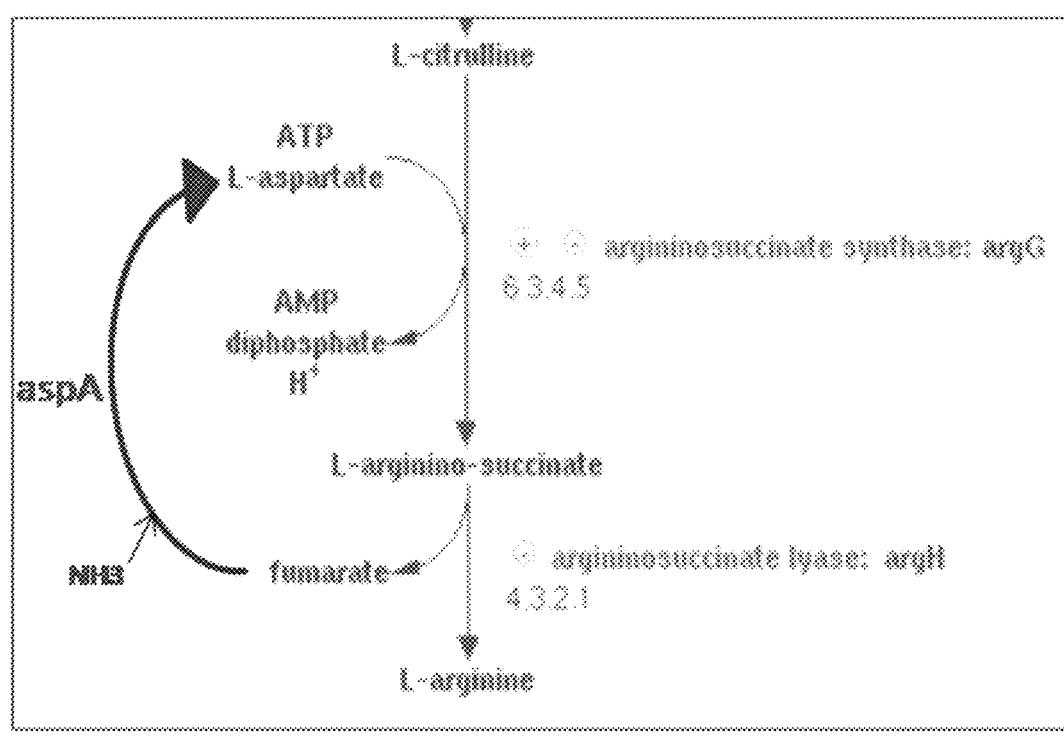

SEQUENCE LISTING

<160> NUMBER OF SEQ ID NOS: 26

<210> SEQ ID NO 1
<211> LENGTH: 38
<212> TYPE: DNA
<213> ORGANISM: Artificial Sequence
<220> FEATURE:
<223> OTHER INFORMATION: primer

<400> SEQUENCE: 1
cgagctcggt acccggggtg tcgcagatgc catcgccg                38

<210> SEQ ID NO 2
<211> LENGTH: 44
<212> TYPE: DNA
<213> ORGANISM: Artificial Sequence
<220> FEATURE:
<223> OTHER INFORMATION: primer

<400> SEQUENCE: 2
cgccaatgac tggctccatg accgcacgaa gggtgtgcac cccg          44

<210> SEQ ID NO 3
<211> LENGTH: 44
<212> TYPE: DNA
<213> ORGANISM: Artificial Sequence
<220> FEATURE:
<223> OTHER INFORMATION: primer

<400> SEQUENCE: 3
cggggtgcac acccttcgtg cggtcatgga gccagtcatt ggcg          44

<210> SEQ ID NO 4
<211> LENGTH: 38
<212> TYPE: DNA
<213> ORGANISM: Artificial Sequence
<220> FEATURE:
<223> OTHER INFORMATION: primer

<400> SEQUENCE: 4
tgcaggtcga ctctagagtt cttgcggtga ccgccacg        38

<210> SEQ ID NO 5
<211> LENGTH: 32
<212> TYPE: DNA
<213> ORGANISM: Artificial Sequence
<220> FEATURE:
<223> OTHER INFORMATION: primer

<400> SEQUENCE: 5
cgagctcggt acccgggttt aactacccc cg               32

<210> SEQ ID NO 6
<211> LENGTH: 36
<212> TYPE: DNA
<213> ORGANISM: Artificial Sequence
<220> FEATURE:
<223> OTHER INFORMATION: primer

<400> SEQUENCE: 6
gtcgactcta gaggatccgg ccatatagtc tgctcc          36

<210> SEQ ID NO 7
<211> LENGTH: 24
<212> TYPE: DNA
<213> ORGANISM: Artificial Sequence
<220> FEATURE:
<223> OTHER INFORMATION: primer

<400> SEQUENCE: 7
ttttggatcc ttttaactac cccc                       24

<210> SEQ ID NO 8
<211> LENGTH: 32
<212> TYPE: DNA
<213> ORGANISM: Artificial Sequence
<220> FEATURE:
<223> OTHER INFORMATION: primer

<400> SEQUENCE: 8
gcaggtcgac tctagacggc catatagtct gc              32

<210> SEQ ID NO 9
<211> LENGTH: 42
<212> TYPE: DNA
<213> ORGANISM: Artificial Sequence
<220> FEATURE:
<223> OTHER INFORMATION: primer

<400> SEQUENCE: 9
ccagtgaatt cgagctcggt acccgggagc tagaacggct gc   42

<210> SEQ ID NO 10
<211> LENGTH: 75
<212> TYPE: DNA
<213> ORGANISM: Artificial Sequence
<220> FEATURE:

```
<223> OTHER INFORMATION: primer

<400> SEQUENCE: 10
ctagctcata tgataaaacg aaaggcccag tctttcgact gagcctttcg ttttatgtat      60
tcactctagc tagcg                                                      75

<210> SEQ ID NO 11
<211> LENGTH: 38
<212> TYPE: DNA
<213> ORGANISM: Artificial Sequence
<220> FEATURE:
<223> OTHER INFORMATION: primer

<400> SEQUENCE: 11
cgttttatca tatgagctag aacggctgca acacatgg                             38

<210> SEQ ID NO 12
<211> LENGTH: 38
<212> TYPE: DNA
<213> ORGANISM: Artificial Sequence
<220> FEATURE:
<223> OTHER INFORMATION: primer

<400> SEQUENCE: 12
gcctgcaggt cgacactagt gtattcactc tagctagc                             38

<210> SEQ ID NO 13
<211> LENGTH: 30
<212> TYPE: DNA
<213> ORGANISM: Artificial Sequence
<220> FEATURE:
<223> OTHER INFORMATION: primer

<400> SEQUENCE: 13
cggaattcga ggaatagagc gggtcataca                                      30

<210> SEQ ID NO 14
<211> LENGTH: 39
<212> TYPE: DNA
<213> ORGANISM: Artificial Sequence
<220> FEATURE:
<223> OTHER INFORMATION: primer

<400> SEQUENCE: 14
gtttctagag ccgggatcct tgataatacg catggccag                            39

<210> SEQ ID NO 15
<211> LENGTH: 41
<212> TYPE: DNA
<213> ORGANISM: Artificial Sequence
<220> FEATURE:
<223> OTHER INFORMATION: primer

<400> SEQUENCE: 15
caaggatccc ggctctagaa acgatggaat ctagcgtcga a                         41

<210> SEQ ID NO 16
<211> LENGTH: 33
<212> TYPE: DNA
<213> ORGANISM: Artificial Sequence
<220> FEATURE:
<223> OTHER INFORMATION: primer

<400> SEQUENCE: 16
aaaactgcag ctttctgttt gtgttgtatt ccc                                  33
```

```
<210> SEQ ID NO 17
<211> LENGTH: 36
<212> TYPE: DNA
<213> ORGANISM: Artificial Sequence
<220> FEATURE:
<223> OTHER INFORMATION: primer

<400> SEQUENCE: 17
gcgtattatc aaggatcctt ccttcaggct aatctt                        36

<210> SEQ ID NO 18
<211> LENGTH: 36
<212> TYPE: DNA
<213> ORGANISM: Artificial Sequence
<220> FEATURE:
<223> OTHER INFORMATION: primer

<400> SEQUENCE: 18
acgaatgttg tttgacatat gtgtttcctt tcgttg                        36

<210> SEQ ID NO 19
<211> LENGTH: 36
<212> TYPE: DNA
<213> ORGANISM: Artificial Sequence
<220> FEATURE:
<223> OTHER INFORMATION: primer

<400> SEQUENCE: 19
caacgaaagg aaacacatat gtcaaacaac attcgt                        36

<210> SEQ ID NO 20
<211> LENGTH: 36
<212> TYPE: DNA
<213> ORGANISM: Artificial Sequence
<220> FEATURE:
<223> OTHER INFORMATION: primer

<400> SEQUENCE: 20
cgacgctaga ttccatcgtt tctagaaact agcata                        36

<210> SEQ ID NO 21
<211> LENGTH: 526
<212> TYPE: PRT
<213> ORGANISM: Corynebacterium glutamicum

<400> SEQUENCE: 21
```

Met Ser Lys Thr Ser Asn Lys Ser Ala Asp Ser Lys Asn Asp Thr
1               5                   10                  15

Lys Ala Glu Asp Ile Val Asn Gly Glu Asn Gln Ile Ala Thr Asn Glu
                20                  25                  30

Ser Gln Ser Ser Asp Ser Ala Ala Val Ser Glu Arg Val Val Glu Pro
        35                  40                  45

Lys Thr Thr Val Gln Lys Lys Phe Arg Ile Glu Ser Asp Leu Leu Gly
    50                  55                  60

Glu Leu Gln Ile Pro Ser His Ala Tyr Tyr Gly Val His Thr Leu Arg
65                  70                  75                  80

Ala Val Asp Asn Phe Gln Ile Ser Arg Thr Thr Ile Asn His Val Pro
                85                  90                  95

Asp Phe Ile Arg Gly Met Val Gln Val Lys Lys Ala Ala Ala Leu Ala
            100                 105                 110

Asn Arg Arg Leu His Thr Leu Pro Ala Gln Lys Ala Glu Ala Ile Val

```
                    115                 120                 125
Trp Ala Cys Asp Gln Ile Leu Ile Glu Glu Arg Cys Met Asp Gln Phe
            130                 135                 140
Pro Ile Asp Val Phe Gln Gly Gly Ala Gly Thr Ser Leu Asn Met Asn
145                 150                 155                 160
Thr Asn Glu Val Val Ala Asn Leu Ala Leu Glu Phe Leu Gly His Glu
                165                 170                 175
Lys Gly Glu Tyr His Ile Leu His Pro Met Asp Asp Val Asn Met Ser
            180                 185                 190
Gln Ser Thr Asn Asp Ser Tyr Pro Thr Gly Phe Arg Leu Gly Ile Tyr
        195                 200                 205
Ala Gly Leu Gln Thr Leu Ile Ala Glu Ile Asp Glu Leu Gln Val Ala
        210                 215                 220
Phe Arg His Lys Gly Asn Glu Phe Val Asp Ile Ile Lys Met Gly Arg
225                 230                 235                 240
Thr Gln Leu Gln Asp Ala Val Pro Met Ser Leu Gly Glu Glu Phe Arg
                245                 250                 255
Ala Phe Ala His Asn Leu Ala Glu Glu Gln Thr Val Leu Arg Glu Ala
                260                 265                 270
Ala Asn Arg Leu Leu Glu Val Asn Leu Gly Ala Thr Ala Ile Gly Thr
            275                 280                 285
Gly Val Asn Thr Pro Ala Gly Tyr Arg His Gln Val Val Ala Ala Leu
        290                 295                 300
Ser Glu Val Thr Gly Leu Glu Leu Lys Ser Ala Arg Asp Leu Ile Glu
305                 310                 315                 320
Ala Thr Ser Asp Thr Gly Ala Tyr Val His Ala His Ser Ala Ile Lys
                325                 330                 335
Arg Ala Ala Met Lys Leu Ser Lys Ile Cys Asn Asp Leu Arg Leu Leu
                340                 345                 350
Ser Ser Gly Pro Arg Ala Gly Leu Asn Glu Ile Asn Leu Pro Pro Arg
            355                 360                 365
Gln Ala Gly Ser Ser Ile Met Pro Ala Lys Val Asn Pro Val Ile Pro
            370                 375                 380
Glu Val Val Asn Gln Val Cys Phe Lys Val Phe Gly Asn Asp Leu Thr
385                 390                 395                 400
Val Thr Met Ala Ala Glu Ala Gly Gln Leu Gln Leu Asn Val Met Glu
                405                 410                 415
Pro Val Ile Gly Glu Ser Leu Phe Gln Ser Leu Arg Ile Leu Gly Asn
            420                 425                 430
Ala Ala Lys Thr Leu Arg Glu Lys Cys Val Val Gly Ile Thr Ala Asn
            435                 440                 445
Ala Asp Val Cys Arg Ala Tyr Val Asp Asn Ser Ile Gly Ile Ile Thr
        450                 455                 460
Tyr Leu Asn Pro Phe Leu Gly His Asp Ile Gly Asp Gln Ile Gly Lys
465                 470                 475                 480
Glu Ala Ala Glu Thr Gly Arg Pro Val Arg Glu Leu Ile Leu Glu Lys
                485                 490                 495
Lys Leu Met Asp Glu Lys Thr Leu Glu Ala Val Leu Ser Lys Glu Asn
            500                 505                 510
Leu Met His Pro Met Phe Arg Gly Arg Leu Tyr Leu Glu Asn
            515                 520                 525

<210> SEQ ID NO 22
```

```
<211> LENGTH: 478
<212> TYPE: PRT
<213> ORGANISM: Escherichia coli

<400> SEQUENCE: 22
```

| | | | | | | | | | | | | | | |
|---|---|---|---|---|---|---|---|---|---|---|---|---|---|---|
|Met|Ser|Asn|Asn|Ile|Arg|Ile|Glu|Glu|Asp|Leu|Leu|Gly|Thr|Arg|Glu|
|1| | | |5| | | | |10| | | | |15| |

Val Pro Ala Asp Ala Tyr Tyr Gly Val His Thr Leu Arg Ala Ile Glu
             20                  25                  30

Asn Phe Tyr Ile Ser Asn Asn Lys Ile Ser Asp Ile Pro Glu Phe Val
         35                  40                  45

Arg Gly Met Val Met Val Lys Lys Ala Ala Met Ala Asn Lys Glu
50                  55                  60

Leu Gln Thr Ile Pro Lys Ser Val Ala Asn Ala Ile Ile Ala Ala Cys
65                  70                  75                  80

Asp Glu Val Leu Asn Asn Gly Lys Cys Met Asp Gln Phe Pro Val Asp
                85                  90                  95

Val Tyr Gln Gly Gly Ala Gly Thr Ser Val Asn Met Asn Thr Asn Glu
            100                 105                 110

Val Leu Ala Asn Ile Gly Leu Glu Leu Met Gly His Gln Lys Gly Glu
        115                 120                 125

Tyr Gln Tyr Leu Asn Pro Asn Asp His Val Asn Lys Cys Gln Ser Thr
    130                 135                 140

Asn Asp Ala Tyr Pro Thr Gly Phe Arg Ile Ala Val Tyr Ser Ser Leu
145                 150                 155                 160

Ile Lys Leu Val Asp Ala Ile Asn Gln Leu Arg Glu Gly Phe Glu Arg
                165                 170                 175

Lys Ala Val Glu Phe Gln Asp Ile Leu Lys Met Gly Arg Thr Gln Leu
            180                 185                 190

Gln Asp Ala Val Pro Met Thr Leu Gly Gln Glu Phe Arg Ala Phe Ser
        195                 200                 205

Ile Leu Leu Lys Glu Glu Val Lys Asn Ile Gln Arg Thr Ala Glu Leu
    210                 215                 220

Leu Leu Glu Val Asn Leu Gly Ala Thr Ala Ile Gly Thr Gly Leu Asn
225                 230                 235                 240

Thr Pro Lys Glu Tyr Ser Pro Leu Ala Val Lys Lys Leu Ala Glu Val
                245                 250                 255

Thr Gly Phe Pro Cys Val Pro Ala Glu Asp Leu Ile Glu Ala Thr Ser
            260                 265                 270

Asp Cys Gly Ala Tyr Val Met Val His Gly Ala Leu Lys Arg Leu Ala
        275                 280                 285

Val Lys Met Ser Lys Ile Cys Asn Asp Leu Arg Leu Leu Ser Ser Gly
    290                 295                 300

Pro Arg Ala Gly Leu Asn Glu Ile Asn Leu Pro Glu Leu Gln Ala Gly
305                 310                 315                 320

Ser Ser Ile Met Pro Ala Lys Val Asn Pro Val Val Pro Glu Val Val
                325                 330                 335

Asn Gln Val Cys Phe Lys Val Ile Gly Asn Asp Thr Thr Val Thr Met
            340                 345                 350

Ala Ala Glu Ala Gly Gln Leu Gln Leu Asn Val Met Glu Pro Val Ile
        355                 360                 365

Gly Gln Ala Met Phe Glu Ser Val His Ile Leu Thr Asn Ala Cys Tyr
    370                 375                 380

Asn Leu Leu Glu Lys Cys Ile Asn Gly Ile Thr Ala Asn Lys Glu Val

```
            385                 390                 395                 400
Cys Glu Gly Tyr Val Tyr Asn Ser Ile Gly Ile Val Thr Tyr Leu Asn
                405                 410                 415

Pro Phe Ile Gly His His Asn Gly Asp Ile Val Gly Lys Ile Cys Ala
                420                 425                 430

Glu Thr Gly Lys Ser Val Arg Glu Val Val Leu Glu Arg Gly Leu Leu
                435                 440                 445

Thr Glu Ala Glu Leu Asp Asp Ile Phe Ser Val Gln Asn Leu Met His
            450                 455                 460

Pro Ala Tyr Lys Ala Lys Arg Tyr Thr Asp Glu Ser Glu Gln
465                 470                 475

<210> SEQ ID NO 23
<211> LENGTH: 1581
<212> TYPE: DNA
<213> ORGANISM: Corynebacterium glutamicum

<400> SEQUENCE: 23
atgtctaaga cgagcaacaa gtcttcagca gactcaaaga atgacgcaaa agccgaagac      60
attgtgaacg gcgagaacca aatcgccacg aatgagtcgc agtcttcaga cagcgctgca     120
gtttcggaac gtgtcgtcga accaaaaacc acggttcaga aaagttccg aatcgaatcg      180 gatctgcttg gtgaacttca gatcccatcc acgcatatt acggggtgca cacccttcgt     240
gcggtggaca acttccaaat ctcacgaacc accatcaacc acgtcccaga tttcattcgc     300
ggcatggtcc aggtgaaaaa ggccgcagct ttagcaaacc gccgactgca cacacttcca     360
gcacaaaaag cagaagcaat tgtctgggct tgtgatcaga tcctcattga ggaacgctgt     420
atggatcagt tccccatcga tgtgttccag ggtggcgcag gtacctcact gaacatgaac     480
accaacgagg ttgttgccaa ccttgcactt gagttcttag ccatgaaaaa gggcgagtac     540
cacatcctgc accccatgga tgatgtgaac atgtcccagt ccaccaacga ttcctaccca     600 actggttttcc gcctgggcat ttacgctgga ctgcagaccc tcatcgctga aattgatgag     660
cttcaggttg cgttccgcca aagggcaat gagtttgtcg acatcatcaa gatgggccgc      720
acccagttgc aggatgctgt tcccatgagc ttgggcgaag agttccgagc attcgcgcac     780
aacctcgcag aagagcagac cgtgctgcgt gaagctgcca accgtctcct cgaggtcaat     840
cttggtgcaa ccgcaatcgg tactggtgtg aacactccag caggctaccg ccaccaggtt     900
gtcgctgctc tgtctgaggt caccggactg gaactaaagt ccgcacgtga tctcatcgag     960
gctacctctg acaccggtgc atatgttcat gcgcactccg caatcaagcg tgcagccatg    1020
aaactgtcca agatctgtaa cgatctacgt ctgctgtctt ctggtcctcg tgctggcttg    1080
aacgaaatca acctgccacc acgcaggct ggttcctcca tcatgccagc caaggtcaac     1140
ccagtgatcc cagaagtggt caaccaggtc tgcttcaagg tcttcggtaa cgatctcacc    1200
gtcaccatgg ctgcggaagc tggccagttg cagctcaacg tcatggagcc agtcattggc    1260
gaatccctct tccagtcact gcgcatcctg ggcaatgcag ccaagacttt gcgtgagaag    1320
tgcgtcgtag aataccgc caacgctgat gtttgccgtg cttacgttga taactccatc     1380
gggattatca cttacctgaa cccattcctg gccacgaca ttggagatca gatcggtaag     1440
gaagcagccg aaactggtcg accagtgcgt gaactcatcc tggaaaagaa gctcatggat    1500
gaaaagacgc tcgaggcagt cctgtccaag gagaacctca tgcacccaat gttccgcgga    1560
aggctctact tggagaacta a                                              1581
```

<210> SEQ ID NO 24
<211> LENGTH: 1437
<212> TYPE: DNA
<213> ORGANISM: Escherichia coli

<400> SEQUENCE: 24

| | | | | | |
|---|---|---|---|---|---|
| atgtcaaaca | acattcgtat | cgaagaagat | ctgttgggta | ccagggaagt | tccagctgat | 60 |
| gcctactatg | tgttcacac | tctgagagcg | attgaaaact | tctatatcag | caacaacaaa | 120 |
| atcagtgata | ttcctgaatt | tgttcgcggt | atggtaatgg | ttaaaaaagc | cgcagctatg | 180 |
| gcaaacaaag | agctgcaaac | cattcctaaa | agtgtagcga | atgccatcat | tgccgcatgt | 240 |
| gatgaagtcc | tgaacaacgg | aaaatgcatg | gatcagttcc | cggtagacgt | ctaccagggc | 300 |
| ggcgcaggta | cttccgtaaa | catgaacacc | aacgaagtgc | tggccaatat | cggtctggaa | 360 |
| ctgatgggtc | accaaaaagg | tgaatatcag | tacctgaacc | cgaacgacca | tgttaacaaa | 420 |
| tgtcagtcca | ctaacgacgc | ctacccgacc | ggtttccgta | tcgcagttta | ctcttccctg | 480 |
| attaagctgg | tagatgcgat | taaccaactg | cgtgaaggct | tgaacgtaa | agctgtcgaa | 540 |
| ttccaggaca | tcctgaaaat | gggtcgtacc | cagctgcagg | acgcagtacc | gatgaccctc | 600 |
| ggtcaggaat | tccgcgcttt | cagcatcctg | ctgaaagaag | aagtgaaaaa | catccaacgt | 660 |
| accgctgaac | tgctgctgga | agttaaccctt | ggtgcaacag | caatcggtac | tggtctgaac | 720 |
| acgccgaaag | agtactctcc | gctggcagtg | aaaaaactgg | ctgaagttac | tggcttccca | 780 |
| tgcgtaccgg | ctgaagacct | gatcgaagcg | acctctgact | gcggcgctta | tgttatggtt | 840 |
| cacggcgcgc | tgaaacgcct | ggctgtgaag | atgtccaaaa | tctgtaacga | cctgcgcttg | 900 |
| ctctcttcag | gcccacgtgc | cggcctgaac | gagatcaacc | tgccggaact | gcaggcgggc | 960 |
| tcttccatca | tgccagctaa | agtaaacccg | gttgttccgg | aagtggttaa | ccaggtatgc | 1020 |
| ttcaaagtca | tcggtaacga | caccactgtt | accatggcag | cagaagcagg | tcagctgcag | 1080 |
| ttgaacgtta | tggagccggt | cattggccag | gccatgttcg | aatccgttca | cattctgacc | 1140 |
| aacgcttgct | acaacctgct | ggaaaaatgc | attaacggca | tcactgctaa | caagaagtg | 1200 |
| tgcgaaggtt | acgtttacaa | ctctatcggt | atcgttactt | acctgaaccc | gttcatcggt | 1260 |
| caccacaacg | gtgacatcgt | gggtaaaatc | tgtgccgaaa | ccggtaagag | tgtacgtgaa | 1320 |
| gtcgttctgg | aacgcggtct | gttgactgaa | gcggaacttg | acgatatttt | ctccgtacag | 1380 |
| aatctgatgc | acccggctta | caaagcaaaa | cgctatactg | atgaaagcga | acagtaa | 1437 |

<210> SEQ ID NO 25
<211> LENGTH: 426
<212> TYPE: PRT
<213> ORGANISM: Corynebacterium glutamicum

<400> SEQUENCE: 25

Met Ser Ser Val Ser Leu Gln Asp Phe Asp Ala Glu Arg Ile Gly Leu
1               5                   10                  15

Phe His Glu Asp Ile Lys Arg Lys Phe Asp Glu Leu Lys Ser Lys Asn
            20                  25                  30

Leu Lys Leu Asp Leu Thr Arg Gly Lys Pro Ser Ser Glu Gln Leu Asp
        35                  40                  45

Phe Ala Asp Glu Leu Leu Ala Leu Pro Gly Lys Gly Asp Phe Lys Ala
    50                  55                  60

Ala Asp Gly Thr Asp Val Arg Asn Tyr Gly Gly Leu Asp Gly Ile Val
65                  70                  75                  80

-continued

```
Asp Ile Arg Gln Ile Trp Ala Asp Leu Leu Gly Val Pro Val Glu Gln
                 85                  90                  95

Val Leu Ala Gly Asp Ala Ser Ser Leu Asn Ile Met Phe Asp Val Ile
            100                 105                 110

Ser Trp Ser Tyr Ile Phe Gly Asn Asn Asp Ser Val Gln Pro Trp Ser
        115                 120                 125

Lys Glu Glu Thr Val Lys Trp Ile Cys Pro Val Pro Gly Tyr Asp Arg
    130                 135                 140

His Phe Ser Ile Thr Glu Arg Phe Gly Phe Glu Met Ile Ser Val Pro
145                 150                 155                 160

Met Asn Glu Asp Gly Pro Asp Met Asp Ala Val Glu Glu Leu Val Lys
                165                 170                 175

Asn Pro Gln Val Lys Gly Met Trp Val Val Pro Val Phe Ser Asn Pro
            180                 185                 190

Thr Gly Phe Thr Val Thr Glu Asp Val Ala Lys Arg Leu Ser Ala Met
        195                 200                 205

Glu Thr Ala Ala Pro Asp Phe Arg Val Val Trp Asp Asn Ala Tyr Ala
    210                 215                 220

Val His Thr Leu Thr Asp Glu Phe Pro Glu Val Ile Asp Ile Val Gly
225                 230                 235                 240

Leu Gly Glu Ala Ala Gly Asn Pro Asn Arg Phe Trp Ala Phe Thr Ser
                245                 250                 255

Thr Ser Lys Ile Thr Leu Ala Gly Ala Gly Val Ser Phe Phe Leu Thr
            260                 265                 270

Ser Ala Glu Asn Arg Lys Trp Tyr Thr Gly His Ala Gly Ile Arg Gly
        275                 280                 285

Ile Gly Pro Asn Lys Val Asn Gln Leu Ala His Ala Arg Tyr Phe Gly
    290                 295                 300

Asp Ala Glu Gly Val Arg Ala Val Met Arg Lys His Ala Ala Ser Leu
305                 310                 315                 320

Ala Pro Lys Phe Asn Lys Val Leu Glu Ile Leu Asp Ser Arg Leu Ala
                325                 330                 335

Glu Tyr Gly Val Ala Gln Trp Thr Val Pro Ala Gly Gly Tyr Phe Ile
            340                 345                 350

Ser Leu Asp Val Val Pro Gly Thr Ala Ser Arg Val Ala Glu Leu Ala
        355                 360                 365

Lys Glu Ala Gly Ile Ala Leu Thr Gly Ala Gly Ser Ser Tyr Pro Leu
    370                 375                 380

Arg Gln Asp Pro Glu Asn Lys Asn Leu Arg Leu Ala Pro Ser Leu Pro
385                 390                 395                 400

Pro Val Glu Glu Leu Glu Val Ala Met Asp Gly Val Ala Thr Cys Val
                405                 410                 415

Leu Leu Ala Ala Ala Glu His Tyr Ala Asn
            420                 425
```

<210> SEQ ID NO 26
<211> LENGTH: 1281
<212> TYPE: DNA
<213> ORGANISM: Corynebacterium glutamicum

<400> SEQUENCE: 26

```
atgagttcag tttcgctgca ggattttgat gcagagcgaa ttggtttgtt ccacgaggac    60
attaagcgca agtttgatga gctcaagtca aaaaatctga agctggatct tactcgcggt   120
aagccttcgt cggagcagtt ggatttcgct gatgagttgt tggcgttgcc tggtaagggt   180
```

```
gatttcaagg ctgcggatgg tactgatgtc cgtaactatg gcgggctgga tggcatcgtt    240
gatattcgcc agatttgggc ggatttgctg ggtgttcctg tggagcaggt cttggcgggg    300
gatgcttcga gcttgaacat catgtttgat gtgatcagct ggtcgtacat tttcggtaac    360
aatgattcgg ttcagccttg gtcgaaggaa gaaaccgtta agtggatttg ccctgttccg    420
ggctatgatc gccatttctc catcacggag cgtttcggct ttgagatgat ttctgtgcca    480
atgaatgaag acggccctga tatggatgct gttgaggaat tggtgaagaa tccgcaggtt    540
aagggcatgt gggttgttcc ggtgttttct aacccgactg gtttcacggt gacagaagac    600
gtcgcaaagc gtctaagcgc aatggaaacc gcagctccgg acttccgcgt tgtgtgggat    660
aatgcctacg ccgttcatac gctgaccgat gaattccctg aggttatcga tatcgtcggg    720
cttggtgagg ccgctggcaa cccgaaccgt ttctgggcgt tcacttctac ttcgaagatc    780
actctcgcgg gtgcgggcgt gtcgttcttc ctcacctctg cggagaaccg caagtggtac    840
accggccatg cgggtatccg tggcattggc cctaacaagg tcaatcagtt ggctcatgcg    900
cgttactttg gcgatgctga gggagtgcgc gcggtgatgc gtaagcatgc tgcgtcgttg    960
gctccgaagt tcaacaaggt tctggagatt ctggattctc gccttgctga gtacggtgtc   1020
gcgcagtgga ctgtccctgc gggcggttac ttcatttccc ttgatgtggt tcctggtacg   1080
gcgtctcgcg tggctgagtt ggctaaggaa gccggcatcg cgttgacggg tgcgggttct   1140
tcttaccgcc tgcgtcagga tccggagaac aaaaatctcc gtttggcacc gtcgctgcct   1200
ccagttgagg aacttgaggt tgccatggat ggcgtggcta cctgtgtgct gttggcagca   1260
gcggagcatt acgctaacta a                                             1281
```

MICROORGANISM OF THE GENUS *CORYNEBACTERIUM* WITH ENHANCED ABILITY TO PRODUCE L-ARGININE AND METHOD FOR PRODUCING L-ARGININE USING THE SAME

CROSS REFERENCE TO RELATED APPLICATIONS

This application is a National Stage Entry of International Application Serial No. PCT/KR2014/003570, filed on Apr. 23, 2014, and claims the benefit of Korean Application No. 10-2013-0044723, filed on Apr. 23, 2013, which is hereby incorporated by reference in its entirety for all purposes as if fully set forth herein.

BACKGROUND OF THE INVENTION

Field of the Invention

The present invention relates to a recombinant microorganism of the genus *Corynebacterium* with an enhanced ability to produce L-arginine, and method for producing L-arginine using the same.

Incorporated by reference herein in its entirety is the Sequence Listing entitled "Sequence list.txt", created Oct. 16, 2015, size of 22 kilobytes.

Description of the Prior Art

L-arginine is contained in garlic or seed of plants as free-form. L-arginine is widely used in medicaments, foods and the like and is also used as an amino acid fortified dietary supplements.

Microorganisms of the genus *Corynebacterium* biosynthesize L-arginine through a cyclic pathway. L-arginine is synthesized from L-glutamate via N-acetylglutamate, N-acetylglutamyl phosphate, N-acetylglutamate semialdehyde, N-acetylornithine, ornithine, citrulline and argininosuccinate.

Further, it is known that *Corynebacterium glutamicum* is regulated by feedback inhibition due to intracellular arginine (Vehary Sakanyan, et al, Microbiology, 142:9-108, 1996), suggesting that the production of L-arginine in high yield is limited.

Ikeda et al. reported that citrulline is accumulated on a fermentation medium during arginine fermentation (Appl Environ Microbiol. 2009 March; 75(6):1635-41. Epub 2009 Jan. 9).

In the biosynthesis process, citrulline binds to aspartate to generate argininosuccinate, which then release fumarate to generate arginine. In this process, aspartate ammonia-lyase (AspA) is an enzyme that synthesizes aspartate from fumarate and ammonia (FIG. 1), and aspartate aminotransferase (AspB) is an enzyme that catalyzes the synthesis of various L-amino acids by transferring the amino group of various L-amino acids such as aspartate, glutamate and aminobutyrate onto the keto-acids such as α-ketoglutaric acid and α-ketoisovaleric acid.

Menkel et al. reported that when *E. coli* aspA was introduced into microorganisms of the genus *Corynebacterium*, the microorganisms of *Corynebacterium* increased the availability of aspatate and then increased lysine production (APPLIED AND ENVIRONMENTAL MICROBIOLOGY, March 1989, p. 684-688).

Accordingly, the present invention provides a microorganism of the genus *Corynebacterium* which has an enhaced ability to produce L-arginine by increasing influx of aspartate that binds to citrulline through the expression enhancement of aspartate ammonia-lyase and/or aspartate aminotransferase

SUMMARY OF THE INVENTION

It is an object of the present invention to provide a microorganism of the genus *Corynebacterium* with an enhanced ability to produce L-arginine.

Another object of the present invention is to provide a method of producing L-arginine using the above microorganism of the genus *Corynebacterium*.

To achieve the above objects, the present invention provides a microorganism of the genus *Corynebacterium* with an enhanced ability to produce L-arginine by enhancement of aspartate ammonia-lyase activity.

The present invention also provides a method of producing L-arginine by culturing the above microorganism of the genus *Corynebacterium*.

BRIEF DESCRIPTION OF THE DRAWINGS

FIG. 1 shows a pathway for synthesizing arginine from citrulline and a pathway for synthesizing aspartate from fumarate.

DETAILED DESCRIPTION OF THE INVENTION

Hereinafter, the present invention will be described in detail.

The present invention provides a microorganism of the genus *Corynebacterium* with an enhanced ability to produce L-arginine.

As used herein, the term "an ability to produce L-arginine (L-arginine productivity)" refers to the ability to accumulate L-arginine in a medium for culturing the microorganism of the genus *Corynebacterium* during culture. Such the ability to produce L-arginine may be either the property of a wild-type or the property imparted or enhanced by artificial mutation, of the microorganisms of the genus *Corynebacterium*.

For example, in order to impart the ability to produce L-arginine, a microorganism of the genus *Corynebacterium* can be breed as a variant having resistance to arginine hydroxamate; a variant having auxotrophy for succinic acid or having resistance to a nucleic acid base analogue; a variant deficient in the ability to metabolize arginine and having resistance to an arginine antagonist and canavanine and auxotrophy for lysine; variant having resistance to arginine, arginine hydroxamate, homoarginine, D-arginine and canavanine, or resistance to arginine hydroxamate and 6-azauracil; or a variant having resistance to canavanine.

In addition, the ability to produce L-arginine can be imparted by modifying a microorganism of the genus *Corynebacterium* so as to increase the expression level of genes encoding enzymes to biosynthesize L-arginine. Examples of enzymes to biosynthesize L-arginine may include N-acetylglutamyl phosphate reductase (ArgC), ornithine acetyl transferase (ArgJ), N-acetylglutamate kinase (ArgB), acetylornithine transaminase (ArgD), ornithine carbamoyl transferase (ArgF), argininosuccinic acid synthetase (ArgG), argininosuccinic acid lyase (ArgH), and carbomyl phosphate synthetase. These enzymes are placed in the Arg operon (argCJBDFRGH) and are regulated by an arginine repressor encoded by argR (J Bacteriol. 2002 December;

184(23):6602-14.). Thus, an ability to produce L-arginine may be imparted by attenuating the arginine repressor (US2002-0045223) or overexpressing at least one of the biosynthesis-related genes.

In the present invention, the microorganism of the genus *Corynebacterium* with an ability to produce L-arginine is not specifically limited as long as it can produce L-arginine. Specifically, it may be *Corynebacterium glutamicum* having the capability to produce L-arginine. More specifically, it may be *Corynebacterium glutamicum* KCCM10741 (Korean Patent Registration No. 10-0791659) or *Corynebacterium glutamicum* ATCC21831), but it's not limited thereof.

In one aspect, the present invention provides a microorganism of the genus *Corynebacterium* with an enhanced ability to produce L-arginine by enhancement of aspartate ammonia-lyase activity.

As used herein, the term "aspartate ammonia-lyase (AspA)" refers an enzyme functioning to synthesize aspartate from fumarate and ammonia, and the synthesis of aspartate may be increased by enhancing the expression of aspartate ammonia-lyase, and thereby L-arginine productivity may be increased by the increased aspartate.

In the present invention, the aspartate ammonia-lyase may be an enzyme derived from any microorganism, as long as it has the aspartate ammonia-lyase activity. Specifically, the aspartate ammonia-lyase may be an enzyme derived from a microorganism of the genus *Escherichia* or the genus *Corynebacterium*. More specifically, it may be an enzyme derived from *E. coli* or *Corynebacterium glutamicum*. Specifically, the aspartate ammonia-lyase may have an amino acid sequence represented by SEQ ID NO: 21 or 22. The *Corynebacterium*-derived aspartate ammonia-lyase having the amino acid sequence represented by SEQ ID NO: 21 is encoded by aspA (NCgl1446) having a nucleotide sequence represented by SEQ ID NO: 23, and the *Escherichia*-derived aspartate ammonia-lyase having an amino acid sequence represented by SEQ ID NO: 22 is encoded by aspA (NCBI GENE ID: 12933698) having a nucleotide sequence represented by SEQ ID NO: 24.

A protein having a homology of at least 80%, specifically at least 90%, more specifically at least 95%, and even more specifically at least 97% to the amino acid sequence of the aspartate ammonia-lyase described above, is also included in the scope of the present invention, as long as it has the aspartate ammonia-lyase activity described in the present invention.

As used herein, the term "homology" refers to the identity between two amino acid sequences and may be determined by the well known method well known to those skilled in the art, using algorithm BLAST (see Karlin and Altschul, Pro. Natl. Acad. Sci. USA, 90, 5873 (1993)) or FASTA (see Pearson, Methods Enzymol., 183, 63 (1990)) to compute the parameter such as score, identity and similarity. Based on the algorithm BLAST, a program called BLASTN or BLASTX has been developed (see gay).

In another aspect, the present invention provides a microorganism of the genus *Corynebacterium*, wherein the activity of aspartate aminotransferase is further enhanced.

As used herein, the term "aspartate aminotransferase" may be derived from a microorganism of the genus *Corynebacterium*, have an amino acid sequence represented by SEQ ID NO: 25 and is encoded by aspB (NCgl0237) having a nucleotide sequence represented by SEQ ID NO: 26, but it's not limited thereto.

A protein having a homology of at least 80%, specifically at least 90%, more specifically at least 95%, and even more specifically at least 97% to the amino acid sequence of the aspartate aminotransferase described above, is also included in the scope of the present invention, as long as it has the aspartate aminotransferase activity described in the present invention. Homology to the amino acid sequence can be determined by, for example, algorithm BLAST (see Karlin and Altschul, Pro. Natl. Acad. Sci. USA, 90, 5873 (1993)) or FASTA (see Pearson, Methods Enzymol., 183, 63 (1990)). Based on this algorithm, a program called BLASTN or BLASTX has been developed (see http://www.ncbi.nlm.nih.gov).

In still another aspect, the present invention provides a microorganism of the genus *Corynebacterium*, wherein activity of aspartate ammonia-lyase and aspartate aminotransferase are both enhanced.

The inventive microorganism of the genus *Corynebacterium* with an ability to produce L-arginine is characterized to be modified by enhancing (or increasing) the activity of aspartate ammonia-lyase and/or aspartate aminotransferase, to the endogenous activity.

As used herein, the term "endogenous activity" refers to the activity of a microorganism of the genus *Corynebacterium* with an ability to produce L-arginine which did not undergo any genetic manipulation or modification for regulating the activities of the above-described enzymes. In addition, the term "enhanced" or "increased" means that L-arginine productivity was improved compared to the endogenous activity of a microorganism of the genus *Corynebacterium* with an ability to produce L-arginine.

Enhancing (or increasing) the activity of the enzyme in the present invention can be performed using various methods well known in the art. Examples of these methods include a method of increasing the copy number of a nucleotide sequence encoding aspartate ammonia-lyase and/or aspartate aminotransferase by introducing a polynucleotide encoding aspartate ammonia-lyase and/or aspartate aminotransferase into a vector system, a method of replacing the promoter with a strong promoter, a method of introducing a mutation into the promoter, and a method based on genetic mutation, but are not limited thereto.

In one specific embodiment of the present invention, in order to enhance the activity of aspartate ammonia-lyase and/or aspartate aminotransferase in the microorganism of the genus *Corynebacterium* with an ability to produce L-arginine, a method may be used in which a copy number of the gene encoding aspartate ammonia-lyase and/or aspartate aminotransferase is increased by introducing the gene encoding aspartated aspartate ammonia-lyase and/or aspartate aminotransferase into a vector and transforming the microorganism of the genus *Corynebacterium* with the vector.

As used herein, the term "transforming" means introducing a vector containing a polynucleotide encoding a target protein into a host cell so that the target protein can be expressed in the host cell. The introduced polynucleotide may be located inside or outside the chromosome of the host cell, as long as it can be expressed in the host cell. The polynucleotide may be introduced in any form, as long as it can be expressed in the host cell.

In an embodiment of the present invention, the transformed microorganism was prepared by introducing the recombinant vector containing the above-described genes, and was then isolating L-arginine-producing strain containing 2 copies of each of the above genes in the chromosome via a second crossover.

As used herein, the term "vector" refers to a DNA construct containing the nucleotide sequence of a target protein-encoding polynucleotide which is operably linked to a suitable regulatory sequence to be able to express the target protein in a suitable host. The regulatory sequence may include a promoter for initiating transcription, any operator sequence for regulating such transcription, a sequence encoding suitable mRNA ribosome binding sites, and sequences which regulate termination of transcription and translation. After being transformed into a suitable host, the vector may be replicated or perform its function irrespective of the host genome, or may be integrated into the genome itself.

The vector that is used in the present invention is not specifically limited, as long as it can be replicated in a host. The vector may be any vector known in the art. Examples of vectors that are commonly used may include natural or recombinant plasmids, cosmids, viruses and bacteriophages.

The *Corynebacterium glutamicum* (KCCM11351P) strain transformed by the method of the present invention is produced by obtaining aspA encoding aspartate ammonia-lyase from the chromosome of L-arginine-producing *Corynebacterium glutamicum* ATCC21831 by PCR, inserting the obtained aspA into a vector, and then introducing the vector into L-arginine-producing *Corynebacterium glutamicum* KCCM10741P and then is a transformed microorganism which has increased expression of aspA. It was found that the strain KCCM11351P can produce L-arginine in high yield by overexpression of aspA.

In yet another aspect, the present invention also provides a method of producing L-arginine by culturing the transformed *Corynebacterium* microorganism.

In the inventive method of producing L-arginine, the process of culturing the transformed microorganism overexpressing L-arginine can be performed in suitable media and culture conditions known in the art. This culture process can be easily adjusted by any person skilled in the art depending on a selected strain. Examples of the culture process include, but are not limited to, batch culture, continuous culture, and fed-batch culture. Such culture processes are disclosed, for example, in "Biochemical Engineering" (James M. Lee, Prentice-Hall International Editions, pp 138-176, 1991).

The medium that is used in the present invention contains raw sugar or glucose as a main carbon source. Further, molasses containing a large amount of raw sugar may also be used as a carbon source. In addition, suitable amounts of various carbon sources may be used, and specifically purified glucose may be used. Examples of a nitrogen source that may be used in the present invention include organic nitrogen sources such as peptone, yeast extract, beef stock, malt extract, corn steep liquor, and soybean flour; and inorganic nitrogen sources such as urea, ammonium sulfate, ammonium chloride, ammonium phosphate, ammonium carbonate, and ammonium nitrate. Specifically, peptone may be used. These nitrogen sources may be used alone or in combination. The medium may contain, as a phosphorus source, potassium dihydrogen phosphate, dipotassium hydrogen diphosphate and corresponding sodium-containing salts. Further, the medium may contain a metal salt such as magnesium sulfate or iron sulfate. In addition, the medium may contain amino acids, vitamins and appropriate precursors. These media or precursors may be added in a batch or continuous manner in the culture. However, the examples of a culture medium composition are not limited thereto.

A compound such as ammonium hydroxide, potassium hydroxide, ammonia, phosphoric acid and sulfuric acid may be added to a culture medium during culture in a suitable manner to adjust the pH of the culture medium. Moreover, a anti-foaming agent such as fatty acid polyglycol ester may be added during culture to inhibit the bubbling. In addition, in order to maintain an aerobic condition of culture medium, oxygen or oxygen-containing gas (e.g., air) may be injected into the culture medium. The temperature of the culture medium may be generally between 20° C. and 45° C., and specifically between 25° C. and 40° C. The culture may be performed until a desired amount of L-arginine is produced. Specifically, the culture time may be 10-160 hours.

Separation of L-arginine from the culture medium can be performed by a conventional method known in the art. The method may include centrifugation, filtration, ion exchange chromatography, and crystallization. For example, L-arginine can be separated by centrifuging the culture medium at low speed to remove biomass, and then separating the remained supernatant by ion exchange chromatography.

Hereinafter, the present invention will be described in further detail with reference to examples. It is to be understood, however, that these examples are for illustrative purposes and are not intended to limit the scope of the present invention.

EXAMPLES

Example 1: Examination of the Effect of aspA on Production of L-Arginine

In order to examine whether aspA is a significant gene in the production of L-arginine, an aspA-deleted vector was constructed and transformed into the L-arginine-producing strain *Corynebacterium glutamicum* KCCM10741P (Korean Patent Registration No. 0791659), and then the L-arginine productivity of the transformed strain was evaluated.

(1) Construction of aspA-Deficient Vector

In order to delete aspA gene encoding aspartate ammonia-lyase (Ncgl1446) from the chromosome, the chromosome of *Corynebacterium glutamicum* ATCC21831 purchased from the American Type Culture Collection (ATCC) was extracted using a Genomic-tip system (QIAGEN), and crossover PCR was performed using chromosome as a template.

Specifically, an about 798-bp fragment having an XmaI restriction enzyme site in the 5' region was amplified by PCR with Pfu polymerase using primers of SEQ ID NOs: 1 and 2 for 30 cycles, each consisting of denaturation at 94 t for 1 min, annealing at 58 t for 30 sec and polymerization at 72 t for 60 sec. Then, an about 829-bp fragment having an XbaI restriction enzyme site in the 3' region was amplified by PCR using primers of SEQ ID NOs: 3 and 4 in the same manner as described above. The resulting DNA fragments were isolated using GeneAll® Expin™ GEL SV kit (Seoul, Korea) and were then used as a template for crossover PCR.

In order to obtain a DNA fragment containing deleted-aspA, crossover PCR was performed using the above-prepared two DNA fragments as a template and primers of SEQ ID NOs: 1 and 4. Specifically, an about 1583-bp fragment was amplified by the above-described PCR method. The amplified fragment was treated with the restriction enzymes XmaI and XbaI, and then ligated with a pD vector treated with the same enzymes, thereby constructing the vector pDKO1446.

(2) Preparation of Recombinant Strain

The pDKO1446 vector constructed as described above was transformed into the L-arginine-producing strain *Corynebacterium glutamicum* KCCM10741P and subjected to a second crossover, thereby obtaining an L-arginineproducing strain containing a deleted-aspA in the chromosome. The obtained strain was named "KCCM10741ΔaspA".

(3) Examination of L-Arginine Productivity of Recombinant Strain

In order to examine the effect of a deletion of aspA on L-arginine productivity, the above-produced recombinant *Corynebacterium glutamicum* KCCM10741ΔaspA that is an L-arginine-producing strain was cultured in the following manner.

As a control group, the host cell, *Corynebacterium glutamicum* KCCM10741P, were used. Specifically, a loop of the strain was inoculated into a 250 ml corner-baffle flask containing 25 ml of the following production medium, and was cultured at 30° C. for 48 hours at 200 rpm. After completion of the culture, the production of L-arginine was measured by HPLC, and the results are shown in Table 1 below.

Production Medium

6% glucose, 3% ammonium sulfate, 0.1% potassium dihydrogen phosphate, 0.2% magnesium sulfate heptahydrate, 1.5% corn steep liquor (CSL), 1% NaCl, 0.5% yeast extract, 100 mg/L biotin, pH 7.2.

TABLE 1

Comparison of L-arginine productivity

| Strain | OD | Arginine concentration (g/L) |
|---|---|---|
| KCCM10741P | 91 | 3.0 |
| KCCM10741PΔaspA | 101 | 2.4 |

As can be seen in Table 1 above, the strain containing a deleted-aspA had a reduced ability to produce L-arginine, and aspA was a significant gene in the production of L-arginine.

Example 2: Construction of Vector for Introducing aspA Derived from *Corynebacterium*

In order to construct a vector containing two copies of aspA (Ncg11446 encoding aspartate ammonia-lyase derived from *Corynebacterium*, PCR was performed using the chromosome of *Corynebacterium glutamicum* ATCC21831 as a template and each of a primer set of SEQ ID NOs: 5 and 6 and a primer set of SEQ ID NOs: 7 and 8, thereby obtaining DNA fragments, each containing aspA.

Specifically, an about 1893-bp fragment having an XmaI restriction enzyme site in the 5' region and a BamHI restriction enzyme site in the 3' region was amplified by PCR with Pfu polymerase using the primers of SEQ ID NOs: 5 and 6. The PCR was performed for 30 cycles, each consisting of denaturation at 94° C. for 1 min, annealing at 58° C. for 30 sec and polymerization at 72° C. for 2 min. Meanwhile, an about 1885-bp fragment having a BamHI restriction enzyme site in the 5' region and an XbaI restriction enzyme site in the 3' region was amplified using the primers of SEQ ID NOs: 7 and 8 in the same manner as described above.

The obtained DNA fragments were separated using Gene-All® Expin™ GEL SV kit (Seoul, Korea). Then, the first fragment of the two fragments above was treated with XmaI and BamHI, and the second fragment was treated with BamHI and XbaI. In addition, a pD vector was treated with XmaI and XbaI. The two DNA fragments and pD vector, treated with the restriction enzymes, were ligated, and thereby constructing a pD1446-2X vector.

Example 3: Preparation of Recombinant Strains Having Increased Expression of aspA The pD1446-2X vector constructed in Example 2 was transformed into each of the L-arginine-producing strains, *Corynebacterium glutamicum* KCCM10741P and ATCC21831, and then subjected to a second crossover, thereby obtaining L-arginine-producing strains containing 2 copies of aspA in the chromosome. The obtained strains were named "KCCM10741P:aspA_2X" and "ATCC21831: aspA_2X", respectively.

Example 4: Construction of Vector for Introducing aspB Derived from *Corynebacterium*

In order to construct a vector containing 2 copies of aspB (Ncg10237) encoding aspartate aminotransferase, PCR was performed using the chromosome of *Corynebacterium glutamicum* ATCC21831 as a template and each of a primer set of SEQ ID NOs: 9 and 10 and a primer set of SEQ ID NOs: 11 and 12, thereby obtaining DNA fragments, each containing aspB.

Specifically, an about 1692-bp fragment having an XmaI restriction enzyme site in the 5' region and a NdeI restriction enzyme site in the 3' region was amplified by PCR with Pfu polymerase using the primers of SEQ ID NOs: 9 and 10. The PCR was performed for 30 cycles, each consisting of denaturation at ° C. for 1 min, annealing at 58° C. for 30 sec and polymerization at 72° C. for 2 min. Meanwhile, an about 1643-bp second fragment having a NdeI restriction enzyme site in the 5' region and a SpeI restriction enzyme site in the 3' region was amplified by the same PCR method as described above.

The obtained DNA fragments were isolated using Gene-All® Expin™ GEL SV kit (Seoul, Korea). Then, the first fragment of the two fragments above was treated with XmaI and NdeI, and the second fragment was treated with NdeI and SpeI. In addition, a pD vector was treated with XmaI and XbaI. The pD vector and the two DNA fragments, which were treated with the restriction enzymes, were subjected to 3-piece ligation, thereby constructing a pD0237-2X vector.

Example 5: Preparation of Strains Having Increased Expression of aspB

The pD0237-2X vector constructed in Example 4 was transformed into each of the L-arginine-producing strains, *Corynebacterium glutamicum* KCCM10741P and ATCC21831, and then subjected to a second crossover, thereby obtaining L-arginine-producing strains containing 2 copies of aspB in the chromosome. The obtained strains were named "KCCM10741P:aspB_2X" and "ATCC21831: aspB_2X", respectively.

Example 6: Preparation of Strains Having Increased Expression of aspA and aspB

The pD0237-2X vector constructed in Example 4 was transformed into each of the recombinant strains (KCCM10741P:aspA_2X and ATCC21831:aspA_2X) prepared in Example 3, and were then subjected to a second crossover, thereby obtaining L-arginine-producing strains containing 2 copies of aspA and aspB in the chromosome.

The obtained strains were named "KCCM10741P:aspA_2X: aspB_2X" and "ATCC21831:aspA_2X:aspB_2X".

Example 7: Evaluation of L-Arginine Productivity

In order to examine the effect of an increase in aspA, aspB or both aspA and aspB on L-arginine productivity, each of the L-arginine-producing strains, *Corynebacterium glutamicum* KCCM10741P:aspA_2X, ATCC21831:aspA_2X, KCCM10741P:aspB_2X, ATCC21831:aspB_2X, KCCM10741P:aspA_2X:aspB_2X and ATCC21831: aspA_2X:aspB_2X, prepared in Examples 3, 5 and 6, was cultured in the following manner.

As a control group, the host cells of each of *Corynebacterium glutamicum* KCCM10741P and ATCC21831 were used. Specifically, a loop of each of the strains was inoculated into a 250-ml corner-baffle flask containing 25 ml of the production medium described in Example 1, and the inoculated strains were cultured at 30° C. for 48 hours at 200 rpm. After completion of the culture, the production of L-arginine was measured, and the results of the measurement are shown in Table 2 below.

TABLE 2

Comparison of arginine productivity between strains

| Strain | OD | Arginine concentration (g/L) |
|---|---|---|
| KCCM10741P | 91 | 3.0 |
| KCCM10741P::aspA_2X | 90 | 3.9 |
| KCCM10741P::aspB_2X | 93 | 3.4 |
| KCCM10741P::aspA_2X::aspB_2X | 93 | 3.7 |
| ATCC21831 | 102 | 4.2 |
| ATCC21831::aspA_2X | 102 | 5.0 |
| ATCC21831::aspB_2X | 105 | 4.7 |
| ATCC21831::aspA_2X::aspB_2X | 104 | 5.1 |

As can be seen in Table 2 above, the production of L-arginine was increased in the two types of the *Corynebacterium glutamicum* strains when 2 copies of aspA was introduced into the strains. Particularly, the L-arginine productivity of KCCM10741P:aspA_2X was remarkably increased by 30% compared to that of the control group. KCCM10741P:aspA_2X was deposited in the Korean Culture Center of Microorganism (KCCM), an international depository authority located at 361-221, Hongje 1-dong Seodaemun-gu, Seoul, Korea, on Jan. 21, 2013 under the accession number KCCM11351P.

Example 8: Construction of Vector for Introducing aspA Derived from the Genus *E. coli*

To introduce aspA (NCBI-GeneID: 12933698), a gene encoding aspartate ammonia-lyase derived from the genus *E. coli*, into the chromosome of *Corynebacterium glutamicum* with an ability to produce L-arginine, a Ncg11221 site known as a glutamate exporter was used (yggB: Appl Environ Microbiol. 2007 July; 73(14):4491-8).

In order to construct a vector having an *E. coli* aspA introduced into the Ncg11221 site, a pDKO1221 vector containing a site-specific gene disruption of Ncg11221 was constructed.

In order to obtain a DNA fragment containing a site-specific gene disruption of Ncg11221, the chromosome of *Corynebacterium glutamicum* ATCC21831 was extracted, and crossover PCR was performed using the chromosome as a template. Specifically, an about 789-bp fragment having an EcoRI restriction enzyme site in the 5' region was amplified by PCR with Pfu polymerase using primers of SEQ ID NOs: 13 and 14. The PCR was performed for 30 cycles, each consisting of denaturation 94° C. for 1 min, annealing at 58° C. for 30 sec and polymerization at 72° C. for 60 sec. Meanwhile, an about 835-bp fragment having a PstI restriction enzyme site in the 3' region was amplified by PCR using primers of SEQ ID NOS: 15 and 16 in the same manner as described above. The obtained DNA fragments were isolated using GeneAll® Expin™ GEL SV kit (Seoul, Korea) and were then used as a template for crossover PCR.

To obtain a DNA fragment containing the site-specific gene disruption of Ncg11221, crossover PCR was performed using the above-obtained two DNA fragments as a template and primers of SEQ ID NOs: 13 and 16. Specifically, an about 1602-bp fragment was amplified by the above-described PCR method. The amplified fragment was treated with the restriction enzymes EcoRI and PstI, and then ligated with a pD vector treated with the same restriction enzymes, thereby constructing a pDKO1221 vector.

Using the constructed pDKO1221 vector, a vector having an *E. coli* aspA introduced therein was constructed. To obtain a cj7 promoter (Korean Patent No. 10-0620092) that operates in *Corynebacterium glutamicum*, an about 524-bp fragment having a BamHI restriction enzyme site in the 5' region was amplified by PCR with Pfu polymerase using p117 pcj7-gfp as a template and primers of SEQ ID NOs: 17 and 18. The PCR was performed for 30 cycles, each consisting of denaturation at 94° C. for 1 min, annealing at 58° C. for 30 sec and polymerization at 72° C. for 30 sec. *E. coli* derived-aspA was extracted from the chromosome of *E. coli* W3110 using a Genomic-tip system (QIAGEN), and an about 1607-bp fragment having an XbaI restriction enzyme site in the 3' region was amplified using the chromosome as a template and primers of SEQ ID NOs: 19 and 20. The obtained DNA fragments were isolated using GeneAll® Expin™ GEL SV kit (Seoul, Korea) and were then used as a template for crossover PCR.

To obtain a DNA fragment of *E. coli* derived-aspA, crossover PCR was performed using the above-obtained two DNA fragments as a template and primers of SEQ ID NOs: 17 and 20. Specifically, an about 2095-bp fragment was amplified by the above-described PCR method. The amplified fragment was treated with the restriction enzymes BamHI and XbaI, and then ligated with a pDKO1221 vector treated with the same restriction enzymes, thereby constructing a pDKO1221-EC_aspA vector.

Example 9: Preparation of Recombinant Strain Having Increased Expression of *E. coli* aspA The pDKO1221-EC_aspA vector constructed as described above was transformed into each of the L-arginine-producing strains *Corynebacterium glutamicum* KCCM10741P and ATCC21831 and subjected to a second crossover, thereby obtaining L-arginine-producing strains, each containing *E. coli* derived-aspA gene in the chromosome. The obtained stains were named "KCCM10741PΔNcg11221-EC_aspA" and "ATCC21831ΔNcg11221-EC_aspA", respectively. In addition, the pDKO1221 vector constructed as described above was transformed into each of the L-arginine-producing strains *Corynebacterium glutamicum* KCCM10741P and ATCC21831 and subjected to a second crossover, thereby obtaining KCCM10741PΔNcg11221 and ATCC21831ΔNcg11221 strains, each containing a deleted NCg11221 in the chromosome.

Example 10: Evaluation of L-Arginine Productivity of Recombinant Strains Having Increased Expression of E. coli aspA In order to evaluate the effect of introduction of E. coli aspA on L-arginine productivity, the L-arginine-producing strains KCCM10741PΔNcg11221-EC_aspA and ATCC21831ΔNcg11221-EC_aspA prepared in Example 9 were cultured in the following manner.

As a control group, the host cells of each of Corynebacterium glutamicum KCCM10741P, ATCC21831, KCCM10741PΔNcg11221 and ATCC21831ΔNcg11221 were cultured. Specifically, a loop of each strain was inoculated into a 250 ml corner-baffle flask containing 25 ml of the above-described production medium and was cultured at 30 t for 48 hours at 200 rpm. After completion of the culture, the production of L-arginine was measured, and the results are shown in Table 3 below.

TABLE 3

Comparison of L-arginine productivity

| Strain | OD | L-Arginine concentration (g/L) |
| --- | --- | --- |
| KCCM10741P | 91 | 3.0 |
| KCCM10741PΔNcg11221 | 90 | 3.0 |
| KCCM10741PΔNcg11221-EC_aspA | 94 | 3.6 |
| ATCC21831 | 102 | 4.2 |
| ATCC21831ΔNcg11221 | 103 | 4.1 |
| ATCC21831ΔNcg11221-EC_aspA | 107 | 4.7 |

As can be seen in Table 3 above, the production of L-arginine in the two types of Corynebacterium glutamicum was increased when E. coli aspA was introduced into the strains. As described above, the present invention provides the recombinant microorganism of the genus Corynebacterium, which has enhanced aspartate ammonia-lyase activity and/or enhanced aspartate aminotransferase activity, and thus has an enhanced ability to produce L-arginine. The recombinant microorganism of the genus Corynebacterium can produce L-arginine in high yield, and thus is industrially useful. From the foregoing, those skilled in the art will appreciate that the present invention may be implemented in other specific forms without departing from the technical spirit or essential characteristics thereof. Accordingly, it should be understood that the above-described embodiments are illustrative in all respects and not restrictive. The scope of the present invention should be defined by the appended claims rather than the detailed description, and it should be appreciated that all the modifications or changes derived from the meaning and scope of the claims and the equivalents thereof fall within the scope of the present invention.

Accession Number

Depository authority: Korean Culture Center of Microorganisms

Accession Number: KCCM11351P

Deposition date: Jan. 21, 2013

What is claimed is:

1. A microorganism of the genus *Corynebacterium* with enhanced ability to produce L-arginine, which is transformed to have an enhanced activity of aspartate ammonia-lyase and aspartate aminotransferase, wherein the aspartate aminotransferase is derived from a microorganism of the genus *Corynebacterium*;

wherein said enhanced activity is obtained by a method selected from:
a) increasing the copy number of a nucleotide sequence encoding aspartate ammonia-lyase and aspartate aminotransferase in said microorganism; or
b) replacing the promoter with a strong promoter in said microorganism.

2. The microorganism of claim 1, wherein the aspartate ammonia-lyase is derived from a microorganism of the genus *Corynebacterium* or a microorganism of the genus *Escherichia coli*.

3. The microorganism according to claim 1, wherein the aspartate ammonia-lyase has an amino acid sequence represented by SEQ ID NO: 21 or 22.

4. The microorganism according to claim 1, wherein the aspartate aminotransferase has an amino acid sequence represented by SEQ ID NO: 25.

5. The microorganism according to claim 1, wherein the microorganism of the genus *Corynebacterium* is *Corynebacterium glutamicum*.

6. A method for producing L-arginine, comprising the steps of:
culturing the microorganism of claim 1 in a culture medium; and
recovering L-arginine from the culture medium.

7. The method of claim 6, wherein the aspartate ammonia-lyase is derived from a microorganism of the genus *Corynebacterium* or a microorganism of the genus *Escherichia coli*.

8. The method according to claim 6, wherein the aspartate ammonia-lyase has an amino acid sequence represented by SEQ ID NO: 21 or 22.

9. The method according to claim 6, wherein the aspartate aminotransferase has an amino acid sequence represented by SEQ ID NO: 25.

10. The method according to claim 6, wherein the microorganism of the genus *Corynebacterium* is *Corynebacterium glutamicum*.

11. The microorganism of claim 1, wherein the method of increasing the copy number of a nucleotide sequence is performed by transformation with vector comprising a polynucleotide encoding aspartate ammonia-lyase and aspartate aminotransferase.

* * * * *